US00PP35217P2

(12) United States Plant Patent
Velazquez

(10) Patent No.: US PP35,217 P2
(45) Date of Patent: Jun. 13, 2023

(54) ***DAPHNE* PLANT NAMED 'MONZULZAY'**

(50) Latin Name: *Daphne odora*
Varietal Denomination: MONZULZAY

(71) Applicant: Monrovia Nursery Company Inc., Azusa, CA (US)

(72) Inventor: Cesar P. Velazquez, Salem, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 17/940,820

(22) Filed: Sep. 8, 2022

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
CPC ..... A01H 5/02; A01H 5/00; A01H 6/00
See application file for complete search history.

(56) References Cited

U.S. PATENT DOCUMENTS

PP28,725 P3 * 12/2017 Velazquez ..... Plt./226

OTHER PUBLICATIONS

Monrovia Banana Split *Daphne* retrieved on Oct. 17, 2022 at https://www.monrovia.com/borealis-variegated-winter-daphne.html, 4 pp. (Year: 2022).*

Trademark Electronic Search System retrieved on Oct. 13, 2022 at https://tmsearch.uspto.gov/bin/showfield?f=doc&state=4807:ezxw10.3.71, 2 pp. (Year: 2022).*

* cited by examiner

*Primary Examiner* — June Hwu
(74) *Attorney, Agent, or Firm* — Cassandra Bright

(57) ABSTRACT

A new and distinct *Daphne* cultivar named 'MONZULZAY' is disclosed, characterized by a distinctive wide bright yellow margin on the foliage. This yellow margin is exceptionally stable and reproduced consistently. The new cultivar is a *Daphne*, suitable for ornamental garden purposes.

2 Drawing Sheets

Latin name of the genus and species: *Daphne odora.*
Variety denomination: 'MONZULZAY'.

BACKGROUND OF THE INVENTION

The new cultivar is a product of a chance discovery in a commercial setting by the inventor. During the Summer of 2015 the inventor, Cesar Velazquez discovered an interesting whole plant mutation in a commercial planting of the unpatented parent variety *Daphne odora* 'Aureomarginata'. The new variety was discovered at a commercial nursery in Dayton, Oreg.

During the Summer of 2015 plants material of the interesting mutation was introduced into a commercial tissue culture laboratory in Dayton, Oreg. The initial propagation showed the mutation to be stable and additional generations were propagated, by semi-hardwood cuttings. Approximately 5 generations have been reproduced since 2015, and have shown that the unique features of this cultivar are stable and reproduced true to type.

SUMMARY OF THE INVENTION

The cultivar 'MONZULZAY' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MONZULZAY' These characteristics in combination distinguish 'MONZULZAY' as a new and distinct *Daphne* cultivar:

1. Wide bright yellow marginal variegation.
2. Stability of bright yellow marginal variegation; reproduced consistently.

COMPARISON TO PARENT VARIETY

Plants of the new cultivar 'MONZULZAY' are similar to plants of the parent; *Daphne odora* 'Aureomarginata' in most horticultural characteristics, however, plants of the new cultivar 'MONZULZAY' differ from the parent variety in the following:

1. 'Aureo-marginata' has subtle and sporadic, yellow-margined foliage whereas 'MONZULZAY' has consistent, larger, more pronounced yellow margins.
2. Yellow marginal color is brighter in the new variety.
3. Variegation is more stable in the new variety in production.

COMMERCIAL COMPARISON

'MONZULZAY' can be compared to the commercial variety *Daphne odora* 'MonStrk', U.S. Plant Pat. No. 28,725. Plants of the new cultivar 'MONZULZAY' are similar to plants of 'MonStrk' in most horticultural characteristics, however, plants of the new cultivar 'MONZULZAY' differ in the following:

1. 'MONZULZAY' has a narrower yellow margin than 'MonStrk'.
2. 'MONZULZAY' has a brighter yellow margin than 'MonStrk'.
3. Variegation is more stable in the new variety.

BRIEF DESCRIPTION OF THE PHOTOGRAPHS

Figure 1:
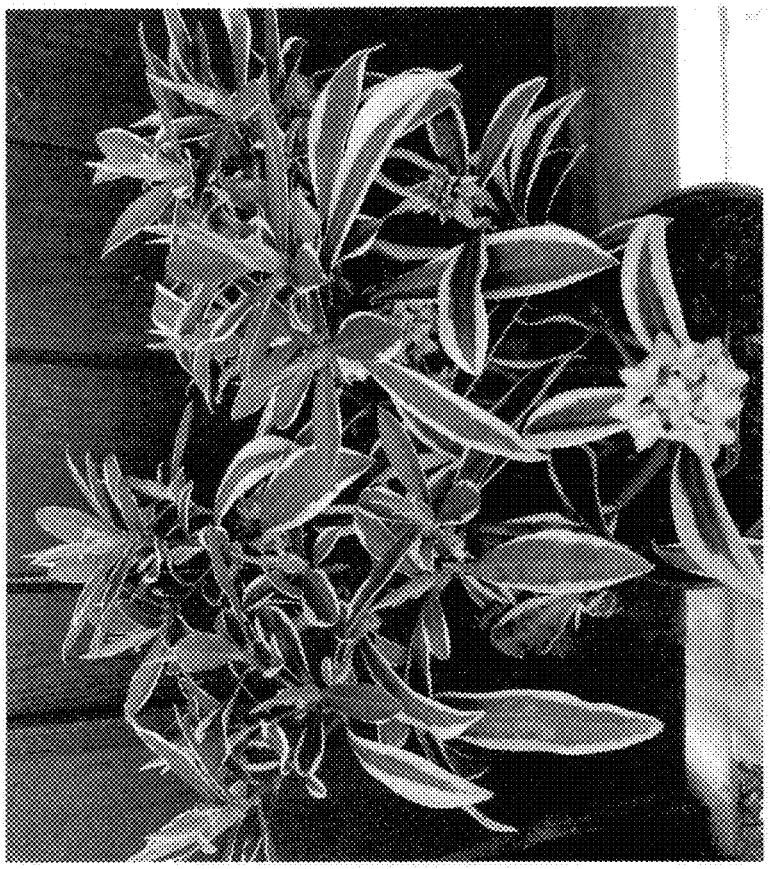

The accompanying photograph in FIG. 1 illustrates in full color a typical plant of 'MONZULZAY' grown outdoors in Oregon.

Figure 2:
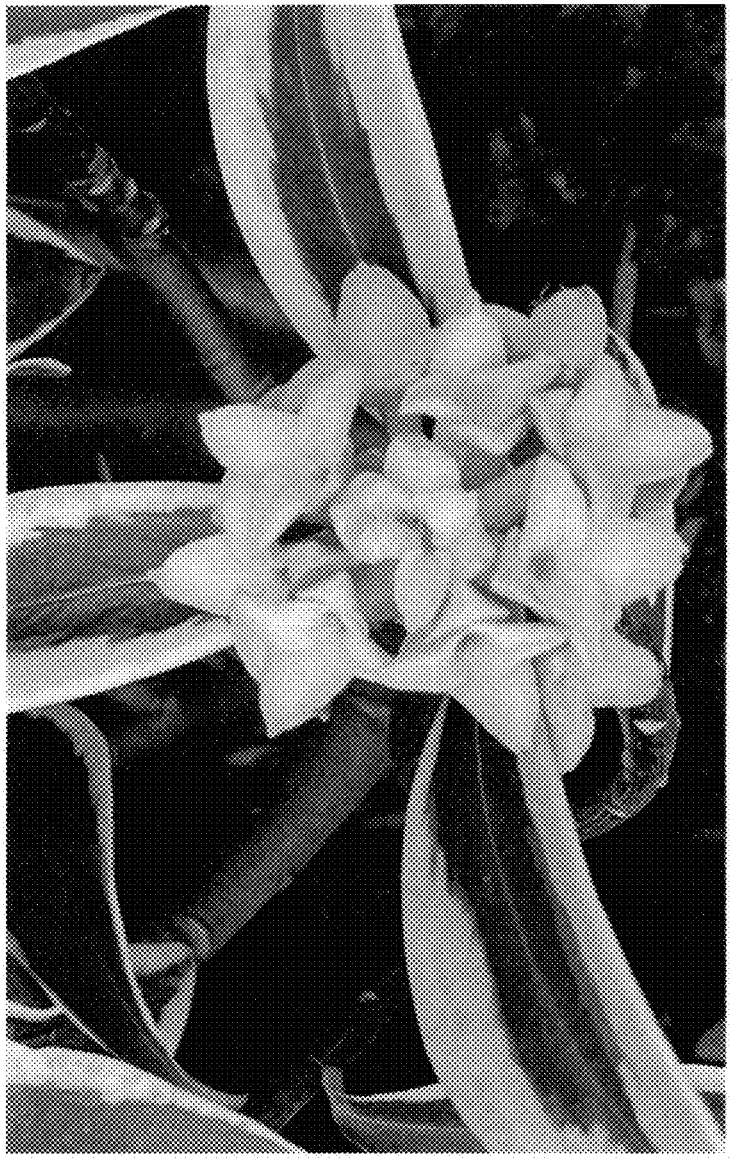

FIG. 2 illustrates in full color a close-up of the foliage and flowers. The plant is approximately 2 years old, and is planted in a 3-gallon pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MONZULZAY' plants grown outdoors in Dayton, Oreg. Plants are approximately 2 to 3 years old, in a 3-gallon nursery container. Temperatures ranged from −8° C. to 20° C. at night to 5° C. to 35° C. during the day. Measurements and numerical values represent averages of typical plant types.

Botanical classification: *Daphne odora* 'MONZULZAY'.

PROPAGATION

Time to rooting: Approximately 4 to 8 weeks at approximately 20° C. to 30° C. from semi-hardwood cuttings.

Root description: Fine, fibrous young roots. Older roots becoming woody. Tan and brown in color, not accurately measured with R.H.S. chart.

PLANT

Growth habit: Strong, bushy, compact deciduous shrub.

Height: Approximately 30 cm.

Plant spread: About 45 cm.

Branching characteristics: 2 to 4 from a pinch.

Characteristics of primary lateral branches:

*Quantity of primary lateral branches.*—3 to 5.

Diameter of lateral branches: Approximately 9 mm.

Lateral branch strength: Very strong, with some flexibility.

Lateral branch color: Young branches near RHS Yellow-Green 145A. Mature branches near RHS Greyed-Green 197A flushed Greyed-Purple 183C.

Other stem or plant characteristics: No pubescence or lenticels observed. Texture very slightly rough, weakly striated.

Lateral branch strength: Very strong, with some flexibility.

Lateral branch color: Young branches near RHS Yellow-Green 145A. Mature branches near RHS Greyed-Green 197A flushed Greyed-Purple 183C.

Other stem or plant characteristics: No pubescence or lenticels observed. Texture very slightly rough, weakly striated.

FOLIAGE

Type: Simple.

*Arrangement.*—Alternate.

*Average length.*—Mature leaf approximately 9.0 to 11.0 cm.

*Average width.*—Average range 2.5 to 3.2 cm.

*Shape of blade.*—Elliptic.

*Apex.*—Acute.

*Base.*—Tapered.

*Attachment.*—Sessile.

*Margin.*—Entire.

*Texture of top surface.*—Smooth.

*Texture of bottom surface.*—Smooth.

*Leaf internode length.*—Approximately 5 to 15 mm.

*Color.*—Young foliage upper side: Near RHS Green 137A with margin near Yellow 10A. Yellow margin comprises about 20% to 30% of the young leaf blade. Young foliage under side: Near RHS Green 138A, lightly streaked 138B. Margin near Yellow 11B. Yellow margin comprises about 20% of the young leaf blade. Mature foliage upper side: Near RHS Green 137A with thick margin (5 mm to 8 mm) near Yellow 10A. Mature foliage under side: Near RHS Green 137B, lightly streaked 138B. Margin near Yellow 10C.

*Venation.*—Type: Pinnate. Venation color upper side: Near RHS Yellow-Green N144A. Venation color under side: Near RHS Yellow-Green N144B.

Petiole: Not present, sessile.

FLOWER

Natural flowering season: Late Winter to Early Spring.

Inflorescence and flower type and habit: Rounded raceme of tightly grouped flowers. Single trumpet shaped flowers composed of petaloid sepals. Corolla not present.

Inflorescence:

*Diameter.*—Approximately 5.0 cm.

*Height.*—Average 3.0 cm.

*Flowers per inflorescence.*—12 to 15.

Individual flower:

*Diameter.*—Approximately 2.2 cm.

*Depth.*—Approximately 1.6 cm.

Persistent or self-cleaning: Self-cleaning.

Fragrance: Very strong sweet scent.

Bud:

*Shape.*—Conical.

*Length.*—8 mm.

*Diameter.*—3 mm.

*Color.*—RHS Purple 76B, flushed Purple N78B and N78C.

Petaloid sepals:

*Quantity.*—4.

*Length.*—Approximately 9 to 13 mm.

*Width.*—Approximately 7 mm.

*Apex.*—Acute to mucronate. Mucronate tip changes to acute with maturity.

*Shape of petal.*—Deltate, slightly rounded.

*Petal margin.*—Entire. Very slightly undulate.

*Petal arrangement.*—Whorled, moderately overlapping.

*Petal texture*.—Smooth, upper and lower surfaces.

*Color*.—Upper surface at first opening: Near RHS Purple 76C, margin 76A. Under surface at first opening: Near RHS Purple 75A and 75B, apex 77A. Upper surface at maturity: Near RHS Purple 76D, margin 76B. Under surface at maturity: Near RHS Purple 77C, 77D streaked Purple 76B.

Corolla tube:

*Length*.—4 mm.

*Diameter*.—3 mm.

*Interior color*.—RHS Red-Purple 69D.

*Exterior color*.—RHS Purple 76D.

*Texture*.—Glabrous.

Pedicels:

*Length*.—2 mm.

*Diameter*.—2 mm.

*Color*.—RHS Yellow-Green 145A.

*Texture*.—Glabrous.

REPRODUCTIVE ORGANS

Stamens:

*Number* (*per flower*).—4.

*Filament length*.—1 mm to 3 mm.

*Anthers*.—Shape: Linear. Length: 1 mm. Color: RHS Greyed-Orange N167C.

Pollen: Moderate quantity, colored near Orange 26A.

Pistils:

*Quantity per flower*.—1.

*Length*.—3 mm.

*Style*.—Length: Less than 1 mm. Color: RHS White N155D.

OTHER CHARACTERISTICS

Fruits and seeds: Not observed to date.

Disease and pest resistance: Not observed to be susceptible nor resistant to normal diseases and pests of *Daphne odora*.

Drought tolerance: No tolerance for drought, extra water required in extremely high temperatures.

Temperature tolerance: USDA Zones 6 to 9.

What is claimed is:

1. A new and distinct cultivar of *Daphne odora* plant named 'MONZULZAY' as herein illustrated and described.

* * * * *